US005502039A

United States Patent [19]

Pier

[11] Patent Number: 5,502,039
[45] Date of Patent: Mar. 26, 1996

[54] O-DERIVATIZED ALGINIC ACID ANTIGENS

[75] Inventor: Gerald Pier, Brookline, Mass.

[73] Assignee: Brigham and Women's Hospital, Inc., Boston, Mass.

[21] Appl. No.: 273,237

[22] Filed: Jul. 11, 1994

Related U.S. Application Data

[63] Continuation-in-part of Ser. No. 962,480, Oct. 16, 1992, abandoned.

[51] Int. Cl.$^6$ .......................... A61K 39/104; C08B 37/00
[52] U.S. Cl. ..................... 514/23; 424/184.1; 424/190.1; 514/779; 514/851
[58] Field of Search .......................... 514/23, 779, 851; 424/184.1, 190.1

[56] References Cited

U.S. PATENT DOCUMENTS

| H494 | 7/1988 | Larrick et al. | 435/172.2 |
|---|---|---|---|
| H1198 | 6/1993 | Larrick et al. | 530/388.4 |
| 2,403,707 | 7/1946 | Cunningham et al. | 536/3 |
| 4,285,936 | 8/1981 | Pier et al. | 536/1.11 |
| 4,349,626 | 9/1982 | Labows et al. | 435/875 |
| 4,446,128 | 5/1984 | Baschang et al. | 424/190.1 |
| 4,490,467 | 12/1984 | Jarman et al. | 435/101 |
| 4,578,458 | 3/1986 | Pier | 536/123 |
| 4,677,070 | 6/1987 | Larrick et al. | 435/240 |
| 4,834,976 | 5/1989 | Rosok et al. | 435/7 |
| 4,873,090 | 10/1989 | Clancy | 424/451 |
| 4,946,677 | 8/1990 | Dorner et al. | 424/92 |
| 4,994,269 | 2/1991 | Collins et al. | 424/85.8 |
| 5,055,455 | 10/1991 | Pier | 514/54 |
| 5,066,794 | 11/1991 | Shiba | 536/4.1 |
| 5,217,872 | 6/1993 | Dorward et al. | 435/7 |
| 5,223,604 | 6/1993 | Hodges et al. | 530/327 |
| 5,233,024 | 8/1993 | Schreiber et al. | 530/387.2 |
| 5,237,053 | 8/1993 | Dorner et al. | 530/387.9 |
| 5,308,761 | 5/1994 | Day et al. | 435/101 |
| 5,324,511 | 6/1994 | Rotering et al. | 530/350 |

FOREIGN PATENT DOCUMENTS 0120532  10/1984  European Pat. Off. .

OTHER PUBLICATIONS

Jennings, H. et al., N–Proprionylated Group B Meningococcal Polysaccharid Mimics A Unique Epitope on Group B Neisseria Meningitis; Apr. 1987; J. Exp. Med., V. 165, pp. 1207–1211.

Bruderer, U. et al., Affinity Constants of Naturally Acquired Healthy Adults and Cystic Fibrosis Patients; J. of Infectious Diseases; 1992 V. 166; pp. 344–349.

Jennings et al., "Induction of Meningococcal Group B Polysaccharide–Specific IgG . . . ", The Journal of Immunology, vol. 137, No. 5, Sep. 1, 1986, pp. 1708–1713.

Cryz, Jr. et al., "Synthesis and Characterization of a Pseudomonas Aeruginosa Alginate–Toxin . . . ", Infection and Immunity, vol. 59, No. 1, Jan. 1991, pp. 45–50.

"Acetylation of Alginic Acid, I. Preparation and Viscosities of Algin Acetates", by R. G. Schweiger, Acetylation of Alginic Acid. II, May 1962, vol. 27, pp. 1786–1789.

"Acetylation of Alginic Acid. II Reaction of Algin Acetates with Calcium and Other Divalent Ions", by R. G. Schweiger, Acetylation of Alginic Acid. II., May 1962. vol. 27, pp. 1789–1791.

"Effect of Acetylation On Some Solution and Gelling Properties of Alginates", by G. Skiak–Braek et al., Carbohydrate Research, 185 (1989), pp. 131–138.

"Selective Acetylation of Mannuronic Acid Residues in Calcium Alginate Gels", by G. Skiak–Braek et al., Carbohydrate Research, 185 (1989), pp. 119–129.

"Monomer Sequence and Acetylation Pattern in Some Bacterial Alginates", by G. Skiak–Braek et al., Carbohydrate Research, 154 (1986), pp. 239–250.

"Protection Against Mucoid *Pseudomonas aeruginosa* In Rodent Models of Endobronchial Infections", by G. B. Pier et al., Science, vol. 249, Aug. 3, 1990, pp. 537–540.

"Alginate of Mucoid Strains of *Ps aeruginosa* in CF", by N. J. Russell et al., pp. 8–91.

*Primary Examiner*—Ronald W. Griffin
*Attorney, Agent, or Firm*—Wolf, Greenfield & Sacks

[57] ABSTRACT

O-derivatized alginic acid antigens capable of eliciting opsonizing antibodies in vivo are described. The O-derivatized antigens show enhanced antigenicity and immunogenicity relative to native, non-O-derivatized alginic acid antigens, particularly the MEP antigen of *p. aeruginosa*. Pharmaceutical compositions containing the O-derivatized antigens of the invention are also described. The invention also pertains to use of the compositions as vaccines, in immunodiagnostic assays, and in methods for producing monoclonal antibodies reactive against the antigen.

Methods for forming O-derivatized alginic acid antigens of the invention are described. A non-O-derivatized starting material is reacted in a solvent with an alkyl anhydride derived from a fatty acid.

29 Claims, 8 Drawing Sheets

O-DERIVATIZED ALGINIC ACID ANTIGENS

This application is a continuation-in-part of U.S. application Ser. No. 07/962,480, filed Oct. 16, 1992, now abandoned, the disclosure of which is incorporated herein by reference.

BACKGROUND OF THE INVENTION

*Pseudomonas aeruginosa* infection is a particularly important problem in patients with cystic fibrosis. More than 70% of patients with cystic fibrosis harbor *P. aeruginosa* in their lungs and up to 90% of cystic fibrosis patients who survive to adulthood have chronic obstructive bronchitis associated with *P. aeruginosa*.

Most of the strains of Pseudomonas isolated from patients with cystic fibrosis produce a peculiar exopolysaccharide that is antigenic and has been characterized as an alginic acid. Production of the exopolysaccharide is observed only among one or two percent of pathogenic Pseudomonas strains isolated from patients without cystic fibrosis. These so-called "mucoid" Pseudomonas strains are considered virtual markers of cystic fibrosis when isolated from a patient with bronchitis.

The exopolysaccharide is believed to contribute to the persistence of the mucoid-generating Pseudomonas strains in the lungs of cystic fibrosis patients. The exopolysaccharide of *Pseudomonas aeruginosa* has, however, been extracted and an exopolysaccharide vaccine capable of inducing an immune response against multiple strains of Pseudomonas has been developed. See Pier, U.S. Pat. No. 4,578,458, the entire contents of which are incorporated herein by reference.

It has been shown that this particular exopolysaccharide, referred to hereinafter as "MEP" antigen, elicits in mice antibodies capable of facilitating opsonization of mucoid *Pseudomonas aeruginosa*, thereby resulting in bacterial death. Nevertheless, these so-called "opsonizing" antibodies are best produced only when certain forms of the MEP is used to immunize mice. Administration of most preparations of MEP at high dosages elicits nonopsonizing antibodies.

In humans, opsonizing antibodies are clearly associated with resistance to mucoid *P. aeruginosa* infection. However, it is difficult to provoke production of opsonizing antibodies in humans by immunizing them with alginic acid-like MEP. One exception is when humans are given 100 μg doses of the largest-sized polymers of MEP. Although induction of opsonizing antibodies is the goal of any MEP vaccine, it would be useful to develop antibodies against *Pseudomonas aeruginosa* that will be opsonizing at all dosage levels and regardless of the size of the particular alginic acid/MEP antigen.

Native MEP alginic acid antigens are composed of a uronic acid polymer backbone, made up of D-mannuronic acid and L-guluronic acid linked together in a beta- 1, 4 linkage. The .polymer backbone carries hydroxyl groups, some of which are derivatized but only with acetic acid. Although both D-mannuronic and L-guluronic acids have hydroxyl groups, acetylation occurs only on the hydroxyl groups of the D-mannuronic acid moieties in native MEP. The hydroxyl groups of the L-guluronic acid are free of acetylation. The degree of acetylation of the native MEP is typically between 2 and 12% by weight, although extremes have been reported where the acetylation is below 2% by weight and up to about 19% by weight in some strains. None are believed optimal for eliciting opsonizing antibodies. There is no acetylation or short chain carboxylic acid derivatization of seaweed alginic acid.

SUMMARY OF THE INVENTION

This invention pertains to alginic acid antigens that have been derivatized with a short chain carboxylic acid to alter the chemical composition from those occurring in nature. They can be made to elicit an immune response characterized by the production of antibodies that bind to microbial pathogens. Preferred antigens elicit antibodies against pathogens of the bacterial genus Pseudomonas, and most preferably to a *Pseudomonas aeruginosa* mucoid exopolysaccharide.

The antigens can be prepared from uronic acid polymers. The uronic acid polymer can be *Pseudomonas aeruginosa* mucoid exopolysaccharide, can be a seaweed uronic acid polymer, or can be virtually any other uronic acid polymer including blocks of D-mannuronic acid. The invention permits the modification of native MEP-alginic acid antigens to enhance their immunogenicity and the construction of useful antigens from polymer backbones obtained from other sources including seaweed. The invention even permits the manufacture of such antigens from starting materials such as mannuronic acid, guluronic acid and short chain carboxylic acids. The O-derivatized alginic acid antigens are formed by the process of derivatizing a uronic acid polymer of. L-guluronic acid and D-mannuronic acid. A variety of products are obtained following this method.

It is desirable that the uronic acid polymer be derivatized with both acetic acid and with one of a nonacetyl short chain carboxylic acids. Preferably the antigen is derivatized between about 2% and 12% by weight with short chain carboxylic acids. The antigen further can comprise a protein covalently linked to the uronic acid polymer, and the antigen can be formulated as a vaccine, preferably for a human.

Native MEP antigen is derivatized only with acetic acid. Derivatization with nonacetyl short chain carboxylic acids can improve native MEP as an antigen. Thus, according to one aspect of the invention, the uronic acid polymer is derivatized with a nonacetyl short chain carboxylic acid. The acid preferably is selected from the group consisting of propionic acid, butyric acid, isobutyric acid, valeric acid and isovaleric acid.

According to another aspect of the invention, the uronic acid polymer is derivatized via a hydroxyl group on a plurality of L-guluronic acid moieties. Native MEP has only its mannuronic acid moieties derivatized, and this aspect of the invention thus distinguishes itself by the derivatization of the L-guturonic acid moieties. The short chain carboxylic acid preferably is selected from the group consisting of acetic acid, propionic acid, butyric acid, isobutyric acid, valeric acid and isovaleric acid. Preferably, at least some of the short chain carboxylic acids are not acetic acid. The uronic acid polymer backbone, extent of derivatization and other aspects can be as set forth above.

Another aspect of the invention is an antigen formed from a uronic acid polymer of L-guluronic acid and. D-mannuronic acid, wherein the L-guluronic acid is present in blocks and wherein the antigen is derivatized with short chain carboxylic acids that are present between about 2% and 12% by weight. This aspect of the invention distinguishes itself from native MEP in that native MEP does not include blocks of guluronic acid. Other uronic acid polymers synthesized ab initio or obtained from seaweed do include such blocks of L-guluronic acid. Other aspects of this antigen including the types of short chain carboxylic acids, linkages with protein and formulations can be as described above.

Still another aspect of the invention involves a method for preparing an antigen capable of eliciting an immune response characterized by the production of antibodies that bind to a *Pseudomonas aeruginosa* mucoid exopolysaccharide. The method involves derivatizing hydroxyl groups of a uronic acid polymer with a short chain carboxylic acid selected from the group consisting of acetic acid, propionic acid, butyric acid, isobutyric acid, valeric acid and isovaleric acid. The uronic acid polymer preferably includes both D-mannuronic and L-guluronic acid moieties. In one aspect of the method, hydroxyl groups of L-guluronic acid moieties are derivatized. In another, those of D-mannuronic acid moieties are derivatized. In yet another, both L-guluronic and D-mannuronic moieties are derivatized with short chain carboxylic acids. As will be clear from the detailed description below, the starting material for the uronic acid polymer may be native *Pseudomonas aeruginosa* mucoid exopolysaccharide or partially or completely deacetylated *Pseudomonas aeruginosa* mucoid exopolysaccharide. The uronic acid polymer also may be obtained from non-bacterial sources such as from seaweed. Likewise, the uronic acid polymer may be synthesized ab initio from purified uronic acids including mannuronic and guluronic acids. A preferred method involves cleaving at least some of the preexisting acetyl derivative from native MEP using a strong base, and then derivatizing this treated MEP with a nonacetyl short chain fatty acid.

The derivatization can occur by reacting the uronic acid polymer and a carboxylic acid anhydride in a solvent for a time sufficient to derivatize hydroxyl groups of the polymer with the carboxylic acid and hydride. The reactants are mixed at a temperature and for time sufficient to form ester linkages with the hydroxyl groups of the uronic acid polymer.

Still another aspect of the invention involves a method for eliciting in an animal antibodies to an alginic acid antigen, comprising administering to an animal an amount of O-derivatized alginic acid antigen prepared according to any of the methods described above or having any of the features described above in an amount effective for eliciting an antibody response in said animal.

The compositions of the invention can be used for preparation of antibodies, for development of immunotherapeutics such as human and murine monoclonal antibodies, or as reagents in immunoassays to detect antibody to mucoid exopolysaccharide (e.g. MEP) in biological fluids. For example, the antigens of the invention and antibodies raised against those antigens can be used in immunoassays to detect the presence or absence of a Pseudomonas strain in a sample taken from a patient. The antigens also can be used as vaccines in humans or in nonhuman mammals such as primates, cows, pigs, horses, goats, sheep, dogs, cats and rodents.

The O-derivatized alginic acid antigens of the present invention can be used, in particular, in pharmaceutical compositions. The pharmaceutical compositions are vaccines containing the O-derivatized antigen in a pharmaceutically effective amount and preferably combined with a pharmaceutically acceptable carrier.

DESCRIPTION OF THE DRAWINGS

FIG. 8A illustrates Ig M response and FIG 8B illustrates Ig G response; (has been added after) FIG. 9A illustrates Ig M response and FIGS. 10A and 10B are graphs that illustrate antigenicity of mouse antibodies elicited by O-propionylated MEP alginic acid antigen; the symbols are identical to those used in FIGS. 8A and 8B. FIG. 10A illustrates Ig M response and FIG. 10B illustrates Ig G response.

DETAILED DESCRIPTION OF THE INVENTION

Compositions of the present invention are alginic acid antigens that have been derivatized with short chain carboxylic acids to alter the chemical composition from those occurring in nature. They can be used to elicit an immune response against microbial pathogens. Preferred antigens elicit antibodies against pathogens of the bacterial genus Pseudomonas.

The term "O-derivatized" refers to alginic acid antigens that have been chemically manipulated by various methods (including those described herein) to artificially change the number and kind of substituents attached to the hydroxyl groups of the antigen. "Non-O-derivatized" alginic acid antigens or "native" alginic acid antigens are those alginic acids occurring in nature that have not been chemically manipulated. Some native alginic acids have O-derivatives. This is exemplified by *Pseudomonas aeruginosa* MEP, which is partially acetylated to about 4.0% by weight. "Non-O-derivatized" or "native" alginic acid antigens as used herein are meant to encompass native MEP, as well as all other naturally-occurring alginic acid antigens.

The O-derivatized alginic acid antigen of the present invention contains substituents that are derived from fatty acid molecules having the general formula RCOOH. A hydroxyl group (OH$^-$) of the alginic acid antigen is esterified with a short chain carboxylic acid to form an "O-derivatized" alginic acid antigen. As used herein, a "short chain carboxylic acid" means a molecule of the formula RCOOH, wherein R is an alkyl group of 1–4 carbons. Esterification can proceed using an anhydride containing a radical having the formula R—C═O⁻, where R can be an alkyl group and can be either saturated or unsaturated, substituted or unsubstituted. Preferred R groups contain 1 carbon (CH3⁻); 2 carbons (CH3(CH2)⁻); 3 carbons (CH3(CH2)$_2$⁻); or 4 carbons (CH3(CH2)$_3$⁻). Thus, the preferred alginic acid antigens of the present invention are O-derivatized with short chain fatty acid moieties derived from acetic acid, propionic acid, butyric acid, isobutyric acid, valeric acid and isovaleric acid.

If derivatizing native MEP, it is preferred to use at least some nonacetyl short chain carboxylic acid. Most preferred is propionic acid. If using completely deacetylated native MEP, uronic acid from seaweed or any other uronic acid without any acetyl derivatization, then it is preferred to derivatize with some acetic acid and some nonacetyl short chain carboxylic acid. It is believed that at least some acetyl derivative must be present to produce effective antigens. The presence of acetyl derivatives may be due to their preexistence on the starting materials or they may be added through the methods described herein. It is believed also that the uronic acid polymer backbone must include blocks of mannuronic acid. A block of an acid is 3 or more monomeric units of one type inked together sequentially.

Thus, as discussed in the Summary above and as shown in the Examples to follow, an antigen may be prepared from, for example, seaweed uronic acid, which antigen is as effective as native MEP. Such an antigen is prepared at a reduced cost over native MEP because of the reduced cost and abundance of the starting material, seaweed. Likewise, the effectiveness of a native MEP antigen can be increased by derivatizing it with a short chain carboxylic acid such as propionic acid. Such derivatization would involve the hydroxyl groups of the guluronic acid subunits, creating an antigen that differs from that in native MEP by both the type of substituent and the location of the substitution.

O-derivatization of the alginic acid antigens of the present invention results in a final antigen having a weight of all short chain carboxylic acid derivative from about 2% to about 12%. The most preferred O-derivatized alginic acid antigen contains greater than a total of about 4% by weight of short chain carboxylic acid derivative.

By "antigen" it is meant a molecule or molecules capable of stimulating an immune response in an animal, which immune response may include both cell-mediated immunity and immunity generated by production of antibodies to the particular antigen.

The O-derivatized alginic acid antigens of the present invention have a polymeric backbone comprised of individual uronic acid monomers. Uronic acids are well-known and well-characterized molecules derived from carbohydrates, in particular C5–C8 acids derived from pentose or hexose monosaccharides. In molecular terms, the preferred O-derivatized alginic acid antigen has a backbone formed of a polymer member of the family of unbranched binary co-polymers of (1→4)-linked beta-D-mannuronic acid and alpha-L-guluronic acid of widely varying composition and sequential structure. See Skjak-Braek, *Biochemistry of Plant Polysaccharides*, pp. 27–33 Biochemical Society Transactions, Volume 20 (1992).

The most preferred O-derivatized alginic acid antigen of the present invention has a polymeric backbone comprised of mannuronic and guluronic acids, the content of mannuronic acid ranging from between about 10% to 100%. Particularly preferred O-derivatized alginic acid antigens have a polymeric backbone comprised of blocks of mannuronic acid. They also can contain blocks of guluronic acid.

Although the preferred O-derivatized alginic acid antigens are polymers with a backbone of mannuronic acid and guluronic acid, other alginic acid backbone polymers may readily be synthesized using standard methods of carbohydrate chemistry and polymer synthesis. The term "alginic acid" is thus meant to include polymers comprising one or more of the other uronic acid monomers. Uronic acid monomers that make up the alginic acid antigens of the present invention can therefore include uronic acids such as D-lyxuronic acid, alpha-D-galacturonic acid, beta-D-galacturonic acid, beta-D-galucuronic acid, D-glucuronic acid, 3-0-methyl, D-glucuronic acid, 4-0-methyl, L-gulurono-3, 6-lactone, L-iduronic acid and alpha D-mannuronic acid.

Non-O-derivatized alginic acid antigens used as starting materials in the present method can be obtained commercially from a number of sources (Sigma Chemical Company, St. Louis, Mo.). Suitable non-O-derivatized alginic acid antigens can also be extracted from seaweeds, primarily the marine brown algae (Phaeophyta) such as Laminaria sp., Macrocystis sp., Fucus sp., Ascophyllum sp, and others. Seaweed is comprised of blocks of guluronic acid as well as blocks of mannuronic acid.

The most preferred non-O-derivatized alginic acid antigen starting materials are of bacterial origin. Bacteria such as *Azotobacter vinlindii* (Skjak-Braek, supra) or *Pseudomonas aeruginosa* MEP are particularly preferred sources of non-O-derivatized alginic acid antigen starting materials. *Pseudomonas aeruginosa* contains blocks of mannuronic acid but not blocks of guluronic acid. *Pseudomonas aeruginosa* is derivatized only on the hydroxyl groups of the mannuronic subunits, but not on the hydroxyl groups of the guluronic subunits. (The mannuronic subunits may be mono- or di-acetylated; di-acetylation occurs less frequently.) It also is derivatized only with acetic acid and not with any detectable levels of any other short chain carboxylic acid. Conversely, the alginic acid antigens of the present invention can be derivatized on the hydroxyl groups .of guluronic (or nonmannuronic) subunits.

Methods of extracting native MEP from Pseudomonas aeruginosa are described in U.S. Pat. No. 4,578,458, the entire contents of which are incorporated herein by reference. The most preferred MEP is produced by *Pseudomonas aeruginosa* 2192 (ATCC No. 39324). This strain produces an MEP having a common immunological determinant capable of inducing a strong immune response against a variety of strains of *Pseudomonas aeruginosa*.

The O-derivatized alginic acid antigens of the present invention show enhanced antigenicity when compared to non-O-derivatized alginic acid antigens such as, for example, the native MEP extracted from *Pseudomonas aeruginosa*, described in U.S. Pat. No. 4,578,458. "Antigenicity" is defined as a relative ability to bind antibodies, and the preferred O-derivatized antigens of the present invention show enhanced binding of antibodies when compared with the binding of antibodies to non-O-derivatized alginic acid antigens.

The O-derivatized alginic acid antigens of the present invention also show enhanced immunogenicity when compared to non-O-derivatized antigens. The term "immunogenicity" is defined as the ability to elicit antibody production in mammals.

A significant feature of the present invention is that the O-derivatized alginic acid antigens of the invention will produce opsonizing antibodies at dosages that are incapable of eliciting opsonizing antibodies in non-O-derivatized alginic acid antigens, particularly those antigens such as native MEP. The term "enhanced immunogenicity" encompasses this characteristic of the present antigens.

Opsonizing antibodies are those antibodies elicited by the present antigens that mediate killing of bacterial pathogens by phagocytosis. The levels of opsonizing antibodies are correlated with the ability of a host to neutralize foreign molecules such as microorganisms by ingesting the microorganisms with macrophages or other cells of the immune system. See generally, *J. Immunology*, 147:1869; see also *Essential Immunol*, I. Roitt, Seventh Edition Blackwell Scientific Publications (1991) and references cited therein for a review of opsonization.

It has been previously shown that native MEP antigen elicits antibodies in mice capable of opsonizing mucoid *P. aeruginosa* for killing by leukocytes and complement, at doses equal to, or less than, 10 micrograms per mouse. Antibodies elicited at higher doses (greater than about 20 micrograms per mouse) were non-opsonic.

In humans, opsonizing antibodies are associated with resistance to mucoid *P. aeruginosa* infection, *N. E. Journal of Medicine*, 317:793–798 (1987). Moreover, in rodents, opsonizing antibodies alone protect against lung infection by mucoid *P. aeruginosa*. Pier et al., *Science*, 249:537–547 (1990).

It has been discovered that the O-derivatized MEP antigens of the present invention elicit opsonizing antibodies even at .doses much greater than 20 micrograms. As will be shown in the Examples, dosages of as low as 1 microgram or as high as 50 micrograms can elicit opsonizing antibodies to the present antigens.

The O-derivatized antigens of the invention can thus be used in pharmaceutical compositions. An exemplary pharmaceutical composition is a vaccine having a therapeutically effective amount of O-derivatized alginic acid antigen optionally included in a pharmaceutically-acceptable and compatible carrier. The term "pharmaceutically-acceptable and compatible carrier" as used herein, and described more fully below, means one or more compatible solid or liquid filler, diluents or encapsulating substances which are suitable for administration to a human or other animal. The term "therapeutically-effective amount" is that amount of the present pharmaceutical compositions which produces a desired result or exerts a desired influence on the particular condition being treated. A "therapeutically-effective amount" of an O-derivatized alginic acid antigen means a percentage concentration of that antigen known in the medical and pharmaceutical arts to be safe and effective in eliciting an antibody response in a subject. Various concentrations may be used in preparing compositions incorporating the same active O-derivatized alginic acid antigen ingredient to provide for variations in the age of the patient to be treated, the severity of the condition, the duration of the treatment and the mode of administration.

In the present invention, the term "carrier" denotes an organic or inorganic ingredient, natural or synthetic, with which the active ingredient is combined to facilitate its application. The term "compatible", as used herein, means that the components of the pharmaceutical compositions are capable of being commingled with the antigen of the present invention, and with each other, in a manner such that there is no interaction which would substantially impair the desired pharmaceutical efficacy.

Dose of the pharmaceutical compositions of the invention will vary depending on the subject and upon particular route of administration used. In general, when used as a vaccine for humans, an overall dose range of from about 1 microgram to about 300 micrograms is contemplated. This dose is delivered on a least two separate occasions, preferably spaced apart by about 4 weeks. Pharmaceutical compositions of the present invention can also be administered to a subject according to a variety of other, well-characterized protocols. For example, certain currently accepted immunization regimens can include the following: (i) Recommended administration times are a first dose at elected date; a second dose at 1 month after first dose; and a third dose at 5 months after second dose. See *Product Information, Physician's Desk Reference*, Merck Sharp & Dohme (1990), at 1442–43. (e.g., Hepatitis B Vaccine-type protocol); (ii) Recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See *Product Information, Physician's Desk Reference*, Merck Sharp & Dohme (1990), at 879 (e.g., Diptheria, Tetanus and Pertussis-type vaccine protocols). Desired time intervals for delivery of multiple doses of a particular O-derivatized alginic acid antigen vaccine can be determined by one of ordinary skill in the art employing no more than routine experimentation.

The O-derivatized alginic acid antigen may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulphuric, nitric, phosphoric, maleic, acetic, salicyclic, p-toluene-sulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise O-derivatized alginic acid antigen off the invention together with one or more pharmaceutically acceptable carriers thereof and optionally any other therapeutic ingredients.

The compositions include those suitable for oral, rectal, topical, nasal, ophthalmic or parenteral administration, all of which may be used as routes of administration using the antigens of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. All methods include the step of bringing the active O-derivatized antigen into association with a carrier which constitutes one or more accessory ingredients. In general, the compositions are prepared by uniformly and intimately bringing the antigen into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the O-derivatized alginic acid antigen in liposomes or as a suspension in an aqueous liquor or non-aqueous liquid such as a syrup, an elixir, or an emulsion.

Preferred compositions suitable for parenteral administration conveniently comprise a sterile aqueous preparation of the O-derivatized antigen, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The O-derivatized alginic acid antigen of the present invention can also be conjugated to a moiety for use in vaccines. The moiety to which the O-derivatized alginic acid antigen is conjugated can be a protein, carbohydrate, lipid, and the like. The chemical structure of this moiety is not intended to limit the scope of the invention in any way. The moiety to which the O-derivatized alginic acid antigen may be bound can also be an adjuvant. The term "adjuvant∞ is intended to include any substance which is incorporated into or administered simultaneously with the O-derivatized alginic acid antigen of the invention which potentiates the immune response in the subject. Adjuvants include aluminum compounds, e.g., gels, aluminum hydroxide and aluminum phosphate gels, and Freund's complete or incomplete adjuvant (in which the O-derivatized alginic acid antigen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), leutinan, pertussis toxin, lipid A, saponins and peptides, e.g., muramyl dipeptide. Rare earth salts, e.g., of lanthanum and cerium, may also be used as adjuvants. The amount of adjuvant required depends upon the subject and the particular O-derivatized alginic acid antigen used and can be readily determined by one skilled in the art without undue experimentation.

For example, an immunizing composition of the present invention can comprise an O-derivatized alginic acid covalently coupled to a protein from a bacteria of the same or different species. An exemplary composition of this type can be an immunizing composition comprising an O-derivatized alginic acid antigen derived from *Pseudomonas aeruginosa*, covalently coupled by means of a linker to a *Pseudomonas aeruginosa* exotoxin A moiety. Other moieties include diphtheria or tetanus toxoid. These antigen-toxin conjugates can be used safely in humans because the toxin is detoxified upon conjugation with the antigen of the invention.

Those of ordinary skill in the art will recognize that a large variety of possible moieties can be linked to the O-derivatized alginic acid antigen of the invention. See, for example, "Conjugate Vaccines", Contributions to Microbiology and Immunology, J. M. Cruse and R. E. Lewis, Jr (eds). Carger Press, New York, (1989), the entire contents of which are incorporated herein by reference.

It will also be appreciated by those of ordinary skill in the art that the O-derivatized alginic acid antigens of the present invention have adjuvant properties by themselves. To the extent that the O-derivatized alginic antigens described herein potentiate human immune responses (see Examples), they can be used as adjuvants in combination with other materials.

The coupling of O-derivatized alginic acid antigen and other moiety (e.g. bacterial protein) can be accomplished by any chemical reaction that will bind the two molecules so long as the antigen retains its immunogenicity and antigenicity and the other moiety retains its activity. This linkage clan include many chemical mechanisms, for instance covalent binding, affinity binding, intercalation, coordinate binding and complexation. The preferred binding is, however, covalent binding. The covalent binding can be achieved either by direct condensation of existing side chains or by the incorporation of external bridging molecules. Many bivalent or polyvalent linking agents are useful in coupling protein molecules, such as the O-derivatized alginic and antigen of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." *Jour. Immun.* 133:1335–2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". *Immunological. Reviews* 62:185–216; and Vitetta et al., supra).

Preferred linkers for coupling a molecular moiety to the O-derivatized antigen are described in the literature.. See, for example, Ramakrishnan, S. et al., *Cancer Res.* 44:201–208 (1984) describing use of MBS (M-maleimido-benzoyl-N-hydroxysuccinimide ester). See also, Umemoto et at. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride (see Example 4, supra); (ii) SMPT (4-succinimidyloxycarbonyl-alpha-methyl-alpha-( 2-pyridyldithio)-toluene (Pierce Chem. Co., Cat. #21558G); (iii) SPDP (succinimidyl-6 [3-(2-pyridyldithio)propionamido] hexanoate (Pierce .Chem. Co., Cat #21651G); (iv) Sulfo-LC-SPDP (sulfosuccinimidyl 6 [3-(2-pyridyldithio)-propianamide] hexanoate (Pierce Chem. Co. Cat. #21650G); and (v) sulfo-NHS (N-hydroxysulfo-succinimide: Pierce Chem. Co., Cat. #24510) conjugated to EDC (see Example 5, supra).

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vivo, resulting in less conjugate available. Sulfo-NHS, in particular, can enhance the stability of carbodiimide couplings. Carbodiimide couplings (such as EDC) when used in conjunction with sulfo-NHS, forms esters that are more resistant to hydrolysis than the carbodiimide coupling reaction alone.

The O-derivatized alginic acid antigens of the invention are also useful in production of monoclonal antibodies. Generally, an animal is immunized with the O-derivatized alginic acid antigen of the invention and a fused cell hybrid is then formed between antibody-producing cells from the immunized animal and an immortalizing cell such as a myeloma.

Mouse, rabbit, or rat anti-O-derivatized alginic acid monoclonal antibodies can be produced by murine, lagomorph, or rodent derived (i.e., mouse, rabbit, rat-derived) hybridomas, which hybridomas are formed by fusion of: (i) a mouse, rabbit or rat myeloma or hybridoma which does not secrete antibody; with (ii) spleen cells from a mouse which secrete antibodies obtained from a mouse immunized against O-derivatized alginic acid antigen. Suitable techniques for producing the antibody moiety are derived from the classic technique of Kohler and Milstein, *Nature:* 256:495 (1975) and are well-known to those of ordinary skill in the art.

Preferred human monoclonal antibodies directed against O-derivatized alginic acid antigen can be produced by directly immortalizing antibody-producing human lymphocytes with Epstein-Barr virus (EBV). Human monoclonal antibodies can also be formed by providing mouse X human fusion partner cell lines that can be fused with an antibody-producing human cell line to generate human monoclonal antibodies. See generally, Larrick et al., U.S. Pat. No. 5,001,065 and references cited therein. See also PCT publication WO93/19197.

In other embodiments, compositions of the invention can be used as reagents in immunoassays to detect antibodies against alginic acid antigens, such as MEP of *Pseudomonas aeruginosa*. Immunoassays can be any of the conventional assay types. For example, a sandwich assay can be performed in which the O-derivatized alginic acid antigen of the invention is affixed to a solid phase. A liquid sample such as a blood-derived fluid or lung fluid containing, or suspected of containing, antibodies directed against MEP of *Pseudomonas aeruginosa* is incubated with the solid phase. Incubation is maintained for a sufficient period of time to allow the antibody in the sample to bind to the immobilized O-derivatized alginic acid antigen on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized O-derivatized alginic acid antigen of the present invention is subsequently incubated with labeled antibody or antibody bound to a coupling agent such as biotin or avidin. Labels for antibodies are well-known in the art and include radionuclides, enzymes, fluors, biotin, and the like. The labeled antibodies are incubated with the solid phase and the label bound to the solid phase is measured, the amount of the label detected serving as a measure of the amount of MEP antibody present in the sample. These and other immunoassays can be easily performed by those of ordinary skill in the art using the present compositions as reagents.

Methods of the invention for forming an O-derivatized alginic acid antigen having enhanced immunogenicity and antigenicity include selecting a suitable non-O-derivatized alginic acid antigen starting material and derivatizing hydroxyl groups of the non-O-derivatized starting material by reacting the starting material with a compound containing a fatty acid moiety of the formula R—C=O$^-$, where R is an akyl group containing from 1 to 4 carbon atoms. After the hydroxyl groups are derivatized, the O-derivatized alginic acid antigen is separated from the other reactants.

One general protocol for O-derivatizing a non-O-derivatized alginic acid antigen starting material includes suspending the non-O-derivatized alginic acid starting material in a non-aqueous solvent, such as benzene or ethylacetate. A particularly preferred solvent is 100% pyridine at a concentration of 2.5 mg/ml or less.

To the mixture of starting material and solvent is added a substantially equal volume of an alkyl or aryl carboxylic acid anhydride of formula $(RCO)_2O$. It is possible to employ solvent percentages less than 100% provided that enough anhydride is added to react with liquid water in the solvent mixture, as well as reacting with the starting material in the reaction mixture. Those of ordinary skill in the art can easily determine the varying percentages of solvent and anhydride that can be used in the present method.

Preferred methods of the present invention result in an ester linkage between the R—C=O$^-$ moiety of the anhydride and the hydroxyl group on the alginic acid polymer backbone. Thus, for adding a two carbon derivative in an ester linkage, acetic anhydride [$(CH3CO)_2O$] is used; for adding a three carbon derivative, propionic anhydride [$(CH3CH2CO)_2O$] is utilized; for adding a four carbon derivative, isobutyric anhydride [$(CH3CH2CH2CO)_2O$] is used. These groups encompass the most preferred derivatives of the present invention.

After the anhydride is added, the material is stirred or otherwise mixed together at a temperature and for a time sufficient to derivatize the hydroxyl groups of the polymer backbone. Mixture of the reactants can be at room temperature although temperatures as high as 100° Centigrade can be employed without deleterious effects and significant reduction in yield. The time or mixing can range from minutes to hours, with a particular range of between 2 minutes to about 48 hours. The preferred conditions for reaction are room temperature for about 48 hours. After reaction, a substantially equal volume of distilled water is added to the mixture to break down any unreacted anhydride material.

The O-derivatized product is then freed from the unreacted material in the mixture using any method that would provide separation, including dialysis against water, ultrafiltration, or precipitation with a water-soluble solvent such as acetone, ethanol or its equivalent. The preferred method of separation of unreacted material is by dialysis. The material can then be recovered from the solvent by lyophilization, may be used directly or may be transferred into other solvents.

Exemplary reaction conditions needed to produce an O-derivatized alginic acid antigen described herein, use 2.0 ml pyridine, 5 mg of MEP starting material and 2.5 ml propionic anhydride. The mixture is stirred for 48 hours at room temperature and unreacted material then is removed.

Another embodiment of the invention further includes a method for removing pre-existing substituents from a non-O-derivatized alginic acid starting material (e.g. native MEP), and then replacing at least those substituents with a different substituent. An exemplary procedure involves removing most acetyl radicals from non-O-derivatized MEP by incubating MEP at high pH and elevated temperatures. One preferred method involves incubating MEP in the presence of a strong base (e.g. 0.1N $NH_4OH$) to raise the pH to about 13.0. The MEP is heated between 50°–100° C. (preferably between 95° C.–100° C.) for between 30 minutes to 5 hours. A particularly preferred heating time is 5 hours. Once most of the acetyl radicals are removed, the MEP is O-derivatized using the methods described herein, using, for example, propionic anhydride.

Introduction of additional fatty acid moieties to non-O-derivatized alginic acid antigens by the methods of the invention results in the presence of 2–12% by weight of these substituents; a minimum of at least 4% being particularly preferred for optimal antigenic and immunogenic activity. Weight determinations of substituents can be carried out using any convenient method, for example quantitative gas chromatography using hydrogen as a carrier gas and a flame ionization detector. An exemplary system is a Hewlett-Packard 5880 gas chromatograph fitted with a Nukol (TM) capillary column (0.53 mm, 25 m long- Alltech Assoc., Waukegen, Ill.). Standardization is carried out with commercial fatty acid standards (Supelco Inc., Bellafonte, Pa.).

The invention will now be illustrated with the following non-limiting examples.

Example 1

Antigenic Properties of O-derivatized Alginic Acid Antigen

Antigenicity analysis

"Antigenicity" is defined as the enhanced reactivity of antibodies to O-derivatized alginic acid antigens of the invention compared with antibody binding to native (i.e. non-O-derivatized) antigen.

Reactivity is measured by enzyme linked immunosorbent assay (ELISA). O-derivatized alginic acid antigen was synthesized using the preferred methods described herein. The antigen was first dissolved at a concentration of 1 to 10 µg per ml of 0.04M phosphate buffer, pH 7.0. Then 0.1 ml of this mixture was added to an ELISA™ plate (Immunolon II from Dynatech, Chantlily Va. or equivalent) and allowed to incubate at 37° C. for 30 to 120 minutes. Plates can be stored overnight at 4° C. if covered.

The solution was then poured off and the plates washed by filling the wells of the plates and emptying them 3 times with a solution of 0.1M phosphate, 0.15M sodium chloride and 0.05% Tween 20 (PBS-t).

The plates were then blocked by adding 0.1–0.2 ml of a solution of 5% skim milk in PBS and incubating; either at 37° C. for 1–3 hours, or overnight at 4° C. The plates were washed three times, as noted above, and then various dilutions of antisera or monoclonal antibody-containing solution added in a volume of 0.1 ml. The diluent was PBS-t-5% skim milk. This primary antibody was diluted in the PBS-t buffer with 5% skim milk added.

The primary antibody was incubated at 37° C. for 1–3 hours, the antibody solution poured off, the plates washed three times as noted above. Then, a dilution in PBS-t with 5% skim milk of a secondary antibody that reacts with the first antibody was added. The secondary antibody was also conjugated to an enzyme such as alkaline phosphatase. The secondary antibody was added in a volume of 0.1 ml. This was reacted at 37° C. for 1–2 hours, the solution poured off and a substrate for the enzyme, such as para-nitro-phenol which is conjugated to the secondary antibody, was then added.

The presence of the antibody was detected by the appearance of a color that results from the activity of the enzyme on the substrate. The concentration of the bound primary antibody was determined by reading the optical density (OD) of the color that results from enzymatic activity. In the case of the alkaline phosphatase enzyme and para-nitrophenol substrate employed here, the wavelength of light used was 405 nm. This was done in an ELISA™ reader.

For these assays, human sera was obtained from patients both pre,- and post-immunization with 100 µg/patient dose of purified MEP human vaccine, lot 2. Sera were obtained from blood drawn 28 days after the injection.

Figure 1:
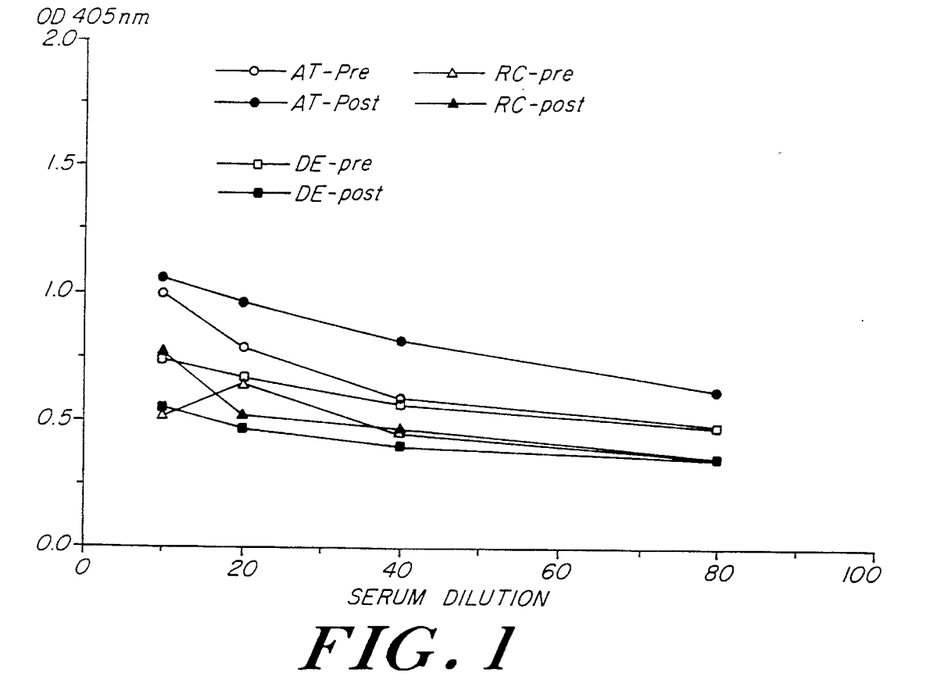
FIG. 1 is a graph that illustrates binding of antibodies in human sera to non-O-derivatized alginic acid antigen.
Figure 2:
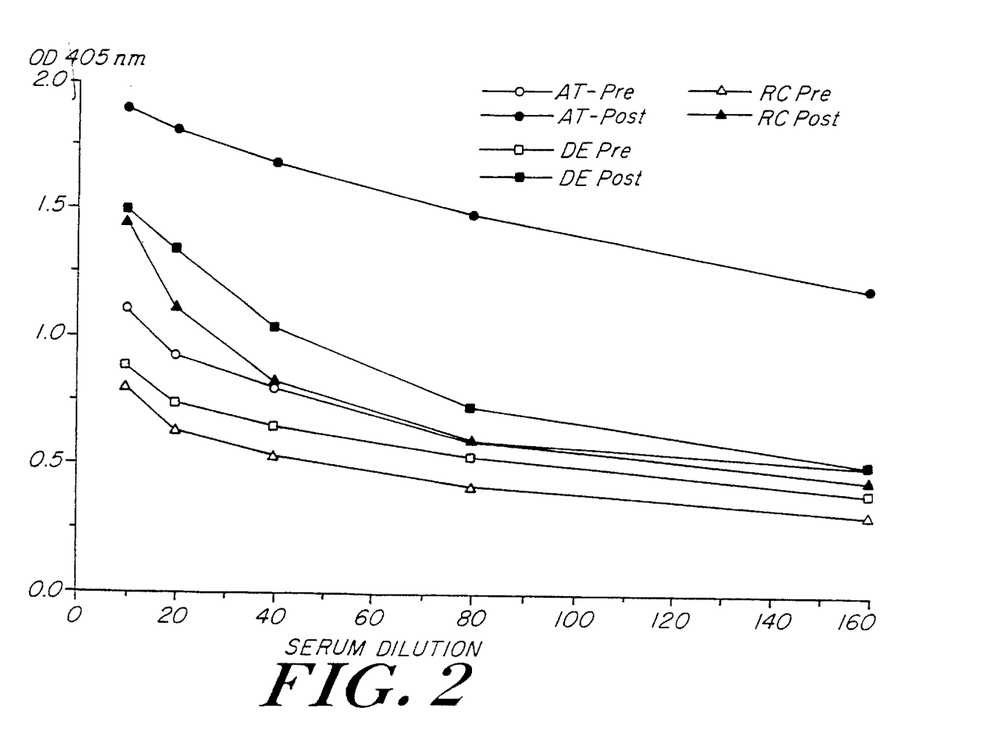
FIG. 2 is a graph that illustrates binding of antibodies in human sera to O-proprionylated MEP alginic acid antigen.

In FIG. 1, antibody binding to the native MEP non-O-derivatized antigen containing 0.25% acetate is illustrated. Antibody binding to an O-propionylated preparation containing ~4.5% propionate is illustrated in FIG. 2. Dilutions of serum ranged from 1:10 up to 1:80 (FIG. 1) or 1:160 (FIG. 2).

With non-O-derivatized native antigen, only 1 sera, AT, showed much of a difference in the antibody binding of post-immunization (solid circles) sera compared with the pre-immunization serum (open circles). Sera from 2 other vaccinates showed no real difference in antibody binding when comparing the post-immunization sample with the pre-immunization sample (RC: closed and open triangles; DE: closed and open squares, respectively).

With O-derivatized alginic acid antigen, antibody binding of the post-immunization samples from the 3 individuals (solid circles, squares and triangles) is higher than the antibody binding of their corresponding pre-immunization samples (open circles, squares, and triangles). Thus, the O-propionylated preparation was better than the non-O-derivatized native preparation at detecting immune responses following immunization of humans With native MEP.

Figure 3:
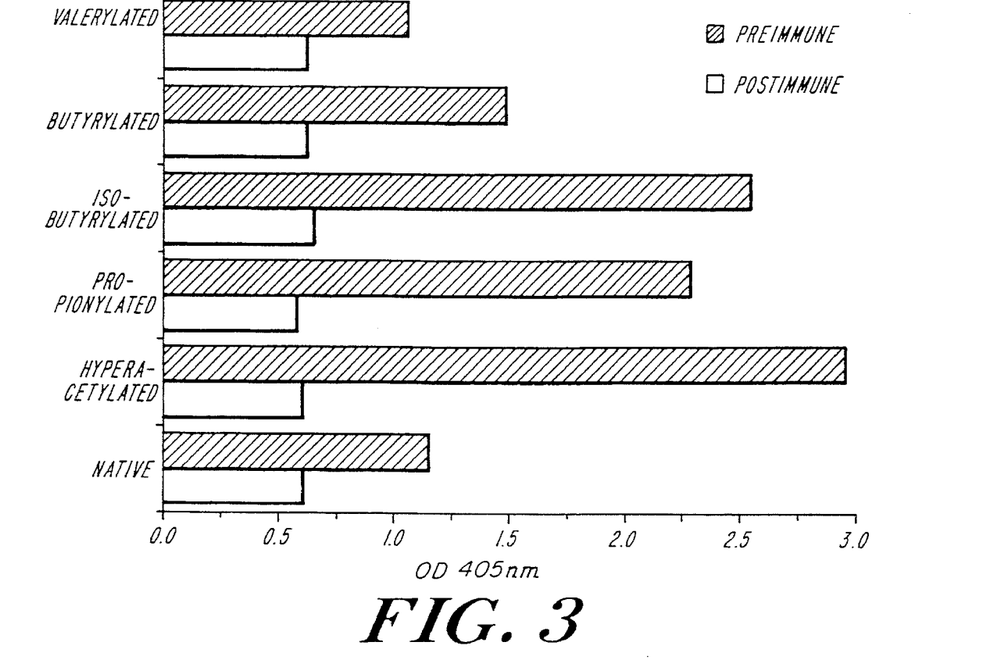
FIG. 3 is a graph that illustrates binding of antibodies in human sera to a variety of O-derivatized MEP alginic acid antigens.

Antibody binding of a single 1:200 dilution of pre- and post-imunization sera (darkened blocks and hatched blocks, respectively) is compared in an experiment (FIG. 3) among a human vaccine to MEP antigen that was O-derivatized with either extra acetate, propionate, isobutyrate, butyrate or valerate. In this experiment, the best antibody binding of the preimmunization serum was seen with the acetylated, propionylated and isobutyrylated preparations, indicating that enhanced antigenicity was observed with higher levels of substitutions using fatty acid moieties with 2 or 3 carbons. When fatty acids with either 4 (butyrylated) or 5 (valerylated) carbons are used, suboptimal results were obtained.

Figure 4:
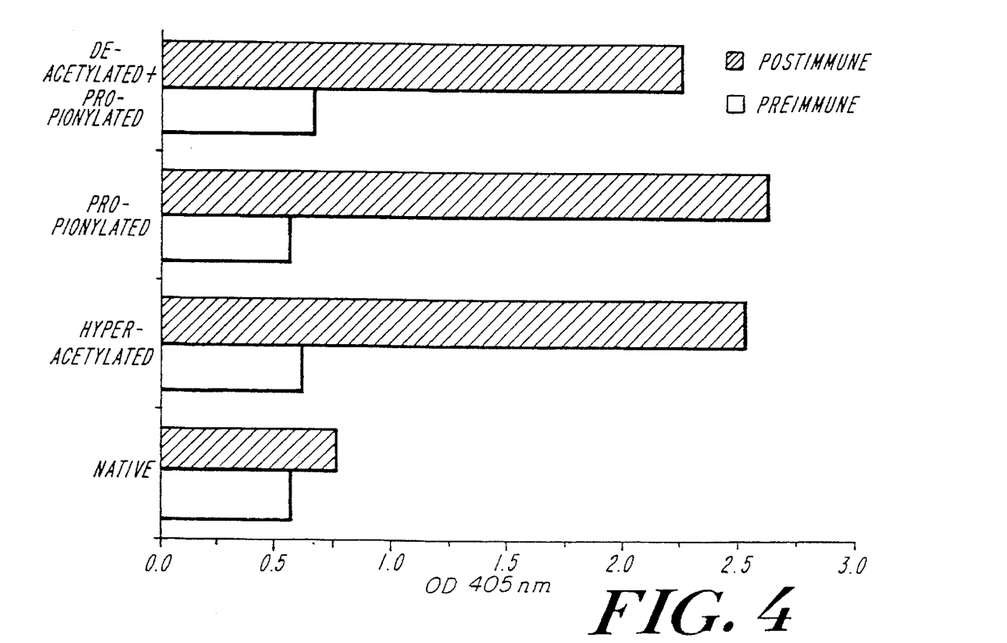
FIG. 4 is a graph that illustrates binding of antibodies in human sera to a variety of O-derivatized alginic acid antigens in a second set of experiments.

In FIG. 4 another preparation (lot) of O-derivatized MEP antigen that was either acetylated; propionylated; or first deacetylated then propionylated, was tested. Again the presence of additional acetate (4% vs. 0.25% in the native non-O-derivatized preparation), propionate, or removal of acetate and replacement with propionate resulted in antigen with enhanced antigenicity, i.e., enhanced binding of antibodies found in the sera relative to vaccination with native MEP.

EXAMPLE 2

Immunogenic Properties of O-derivatized Alginic Acid Antigen

C3H/HeN background mice (Harlan Sprague Dawley, Inc., Indianapolis, Ind.) were immunized intraperitoneally with the indicated dosage of non-o-derivatized antigen (i.e.

MEP antigen) or o-derivative dissolved in a 0.2 ml volume of sterile saline or other suitable buffer. Blood was obtained by nicking the tail with a scalpel or razor just before immunization and at 6–8, 13–15, 20–22, 27–29 and 33–35 days thereafter. Serum was recovered from clotted blood and stored at −20° C. until the opsonophagocytosis assay.

Assay for opsonizing antibodies

The basic method was described by Ames et al., "Opsonophagocytic killing activity of rabbit antibody to *Pseudomonas aeruginosa* mucoid exopolysaccharide", *Infection and Immunity* 49:281–285 (1985). Human leukocytes (white blood cells) were isolated from blood obtained from a vein in the arm of a volunteer. Blood (10–50 ml) was drawn into a syringe, then mixed with an equal volume of 10% dextran T-500 in citrate buffer. The red blood cells were allowed to settle out and the leukocyte rich upper layer drawn off. The white cells were recovered by centrifugation (1000× g, 10 minutes), washed twice in RPMI 1640 medium, then resuspended in 1% ammonium chloride for 10 minutes to lyse remaining cells. The white cells were again recovered by centrifugation as above and resuspended in RPMI 1640 medium containing 15% fetal bovine serum. The concentration of the leukocytes was determined by counting in a hemocytometer and adjusted to a concentration of $2 \times 10^7$/ml.

A second component of the assay is bacteria, obtained by inoculating a growth of mucoid *P. aeruginosa* (strain 2192 or any other suitable strain) from a tryptic soy agar (or other suitable medium) plate prepared the night before and incubated at 37° C. into a 10 ml tube of tryptic soy broth (or other suitable medium). The initial concentration of bacteria was determined to give a reading of 0.1 optical density (OD) units at 650 nm wavelength light in a 1.25 cm diameter spectrophotometer tube. This is approximately $10^8$ cfu/ml.

The tube was held at 37° C. and the bacteria allowed to grow until an OD at 650 nm of 0.4 was obtained, corresponding to about $4 \times 10^9$ cfu/ml. The bacteria were spun down by centrifuging at 2000×g for 10 minutes and resuspended in 10 ml of RPMI 1640 medium. This was then diluted 1:200 into RPMI 1640 medium with 15% fetal bovine serum to give a concentration of bacteria of ~$2 \times 10^7$ cfu/ml.

The third component of the assay is fresh normal human serum to serve as a source of complement. Fresh serum was diluted 1:15 in RPMI 1640 medium with 15% fetal bovine serum. The remaining component of the assay is the antibody in the serum of the immunized mice, diluted 1:2 or higher in RPMI 1640 medium with 15% fetal bovine serum.

One-hundred µl of each of the 4 components (human leukocytes, bacteria, complement, and antibody) were combined in 1.5 ml microfuge tube with a closable cap. Most antibody preparations were tested in duplicate. Controls include an antibody source known to contain opsonizing antibodies (positive control), and a source known to lack opsonic antibodies (negative control) and a tube without any antibody at all, but 0.1 ml of RPMI 1640 medium with 15% bovine serum in place of antibody.

To enumerate the number of bacteria present at the beginning of the assay, 25 µl aliquots were removed from 2–6 random tubesN Each 25 µl aliquot was diluted into 225 µl of sterile water. This was further diluted 10 fold into sterile saline (1:100 dilution) and this dilution is again diluted 10 fold (1:1000 dilution) into sterile saline. From the $10^{-2}$ and $10^{-3}$ dilutions, 10 µl amounts were removed and individually placed onto the end of a tryptic soy agar plate. Four such 10 µl drops can be accommodated by a standard plate.

The plate was then held perpendicular to the ground to allow the 10 µl drop to run down the plate. The plates were then placed at 37° C., as were the tubes containing the assay. The tubes were rotated end over end for 90 minutes. At this time, they were removed from the 37° C. incubator.

From each tube, 25 ul was removed and placed in 225 ul sterile water. Dilutions and platings for bacterial enumerations were performed, as described above. The next day (18–24 hr at 37° C.) plates were removed, bacterial colonies counted, and the average of the counts for identical tubes determined. The percent kill of bacteria was then calculated as follows:

% kill=100−[(cfu in post-immunization sample/cfu in preimmunization sample)×100].

We have used ≧50% kill as representative of biologically plausible, significant killing level. Thus, a serum dilution that mediates ≧50% kill is termed positive for opsonic killing antibody. An opsonic titer is defined as the highest serum dilution mediating ≧50% killing of bacteria.

Figure 5:
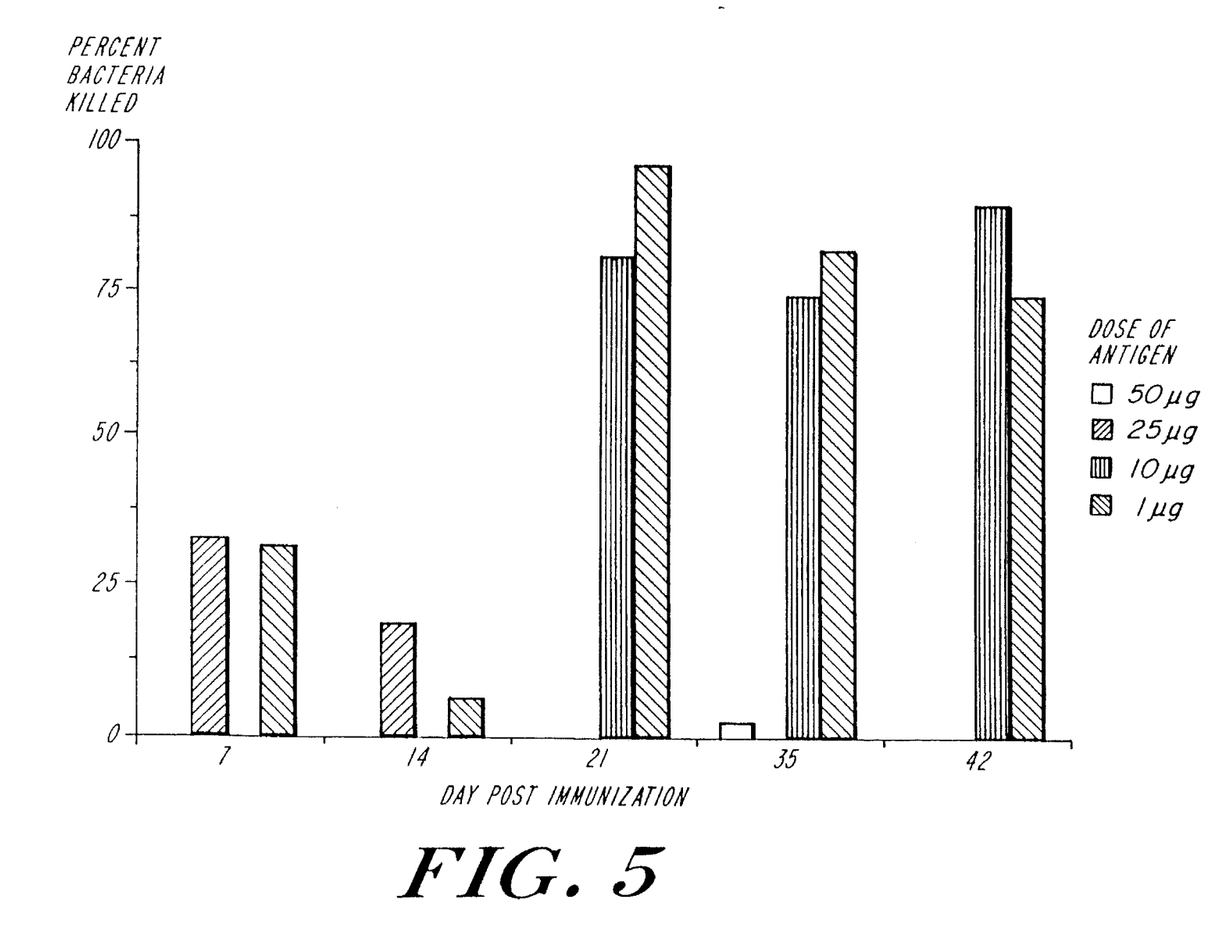
FIG. 5 is a graph that illustrates bacterial killing by antibodies elicited by native MEP antigen at various dosages: ▨1 ug; ▥10 ug; ▧25 ug; and □ 50 ug.
Figure 6:
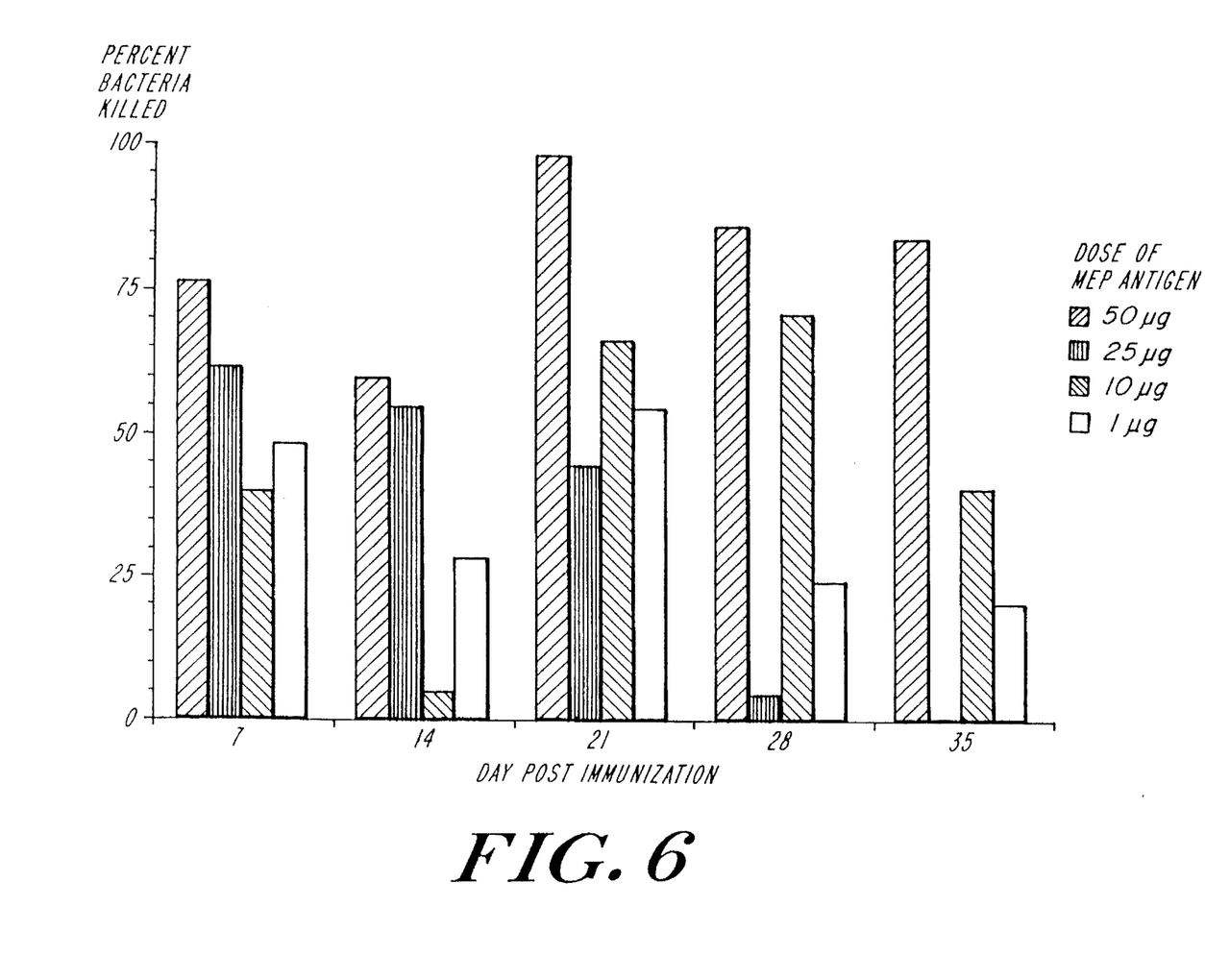
FIG. 6 is a graph that illustrates bacterial killing by antibodies elicited by O-derivatized MEP alginic acid antigen at the same dosages shown in FIG. 5.
Figure 7:
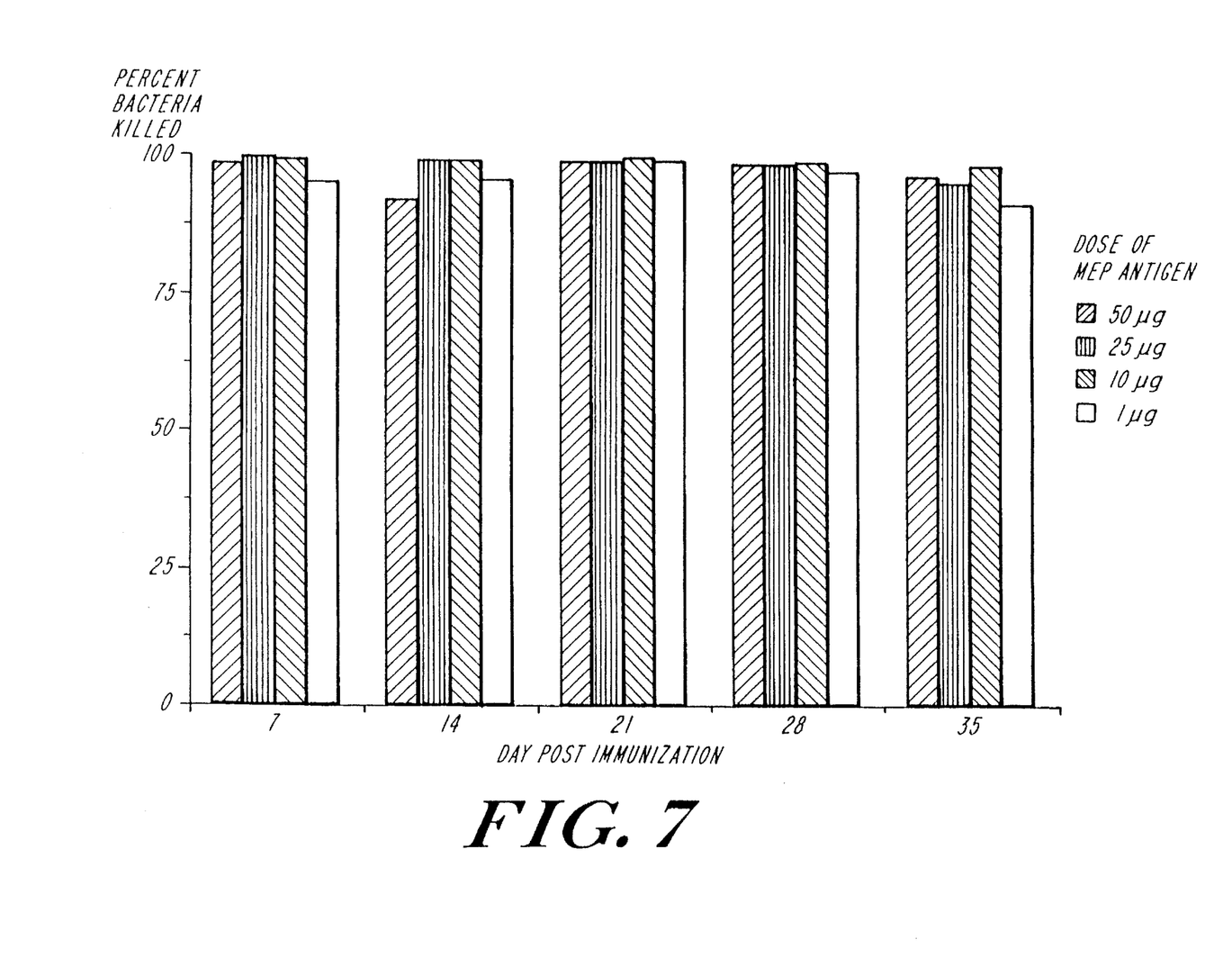
FIG. 7 is a graph that illustrates bacterial killing by antibodies elicited by another O-derivatized MEP alginic acid antigen at the same dosages as shown in FIG. 5

Results i. Opsonizing antibodies. Results in FIGS. 5–7 are for a final Serum dilution of 1:8. In FIG. 5 is shown the presence of opsonic killing antibody elicited in mice by native, non-O-derivatized MEP antigen (lot 0075). Consistent with previous reports using other lots of non-O-derivatized MEP antigen, Garner et al., . "Immunogenic properties of *Pseudomonas aeruginosa* mucoid expolysaccharide", *Infection and Immunity* 58:1835–1842 (1990), low doses of 1 and 10 µg/mouse elicited opsonizing antibodies after 2 doses (given on day 0 and 14), while higher doses do not provoke antibodies.

In FIG. 6, the results using MEP antigen (lot 0075) with increased amounts of acetate substituents (non-O-derivatized: 1.3% acetate; O-acetylated: 7.2% acetate).

Enhanced immunogenicity was measured by development of opsonizing killing antibodies, particularly at the 50 µg/mouse dose. In FIG. 7 we show the results using O-derivatized antigen (MEP lot 0075 as starting material) containing 4.5% propionate by weight. At all doses and on all days there are high levels of opsonizing antibody, indicating enhanced development of these antibodies following immunization by O-derivatized MEP.

Table I shows the titer or dilution of mouse serum giving ≧50% kill following immunization with different preparations of native MEP and O-derivatized MEP. The serum obtained on day 28 or 35 was used.

| Preparation | Dose (µg) | Final serum dilution Giving ≧50% bacterial kill |
|---|---|---|
| Native (Non-O-derivatized) | 1 | 8 |
|  | 10 | 8 |
|  | 25 | NK* |
|  | 50 | NK |
| Acetylated | 1 | NK |
|  | 10 | NK |
|  | 25 | NK |
|  | 50 | 32 |
| Propionylated | 1 | ≧64 |
|  | 10 | >64 |
|  | 25 | 32 |
|  | 50 | 32 |

*NK-no killing

Figure 8A:
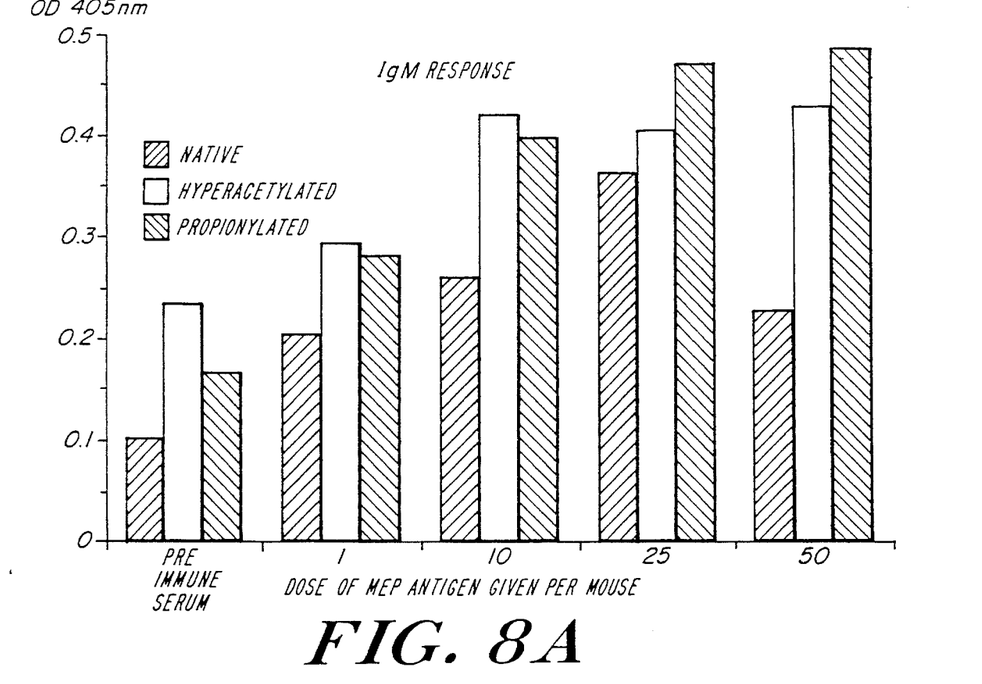
FIG. 8A and 8B are graphs that illustrate antigenicity of mouse antibodies elicited by native MEP alginic acid antigen, the type of alginic acid antigen used to coat She test plate being non-O-derivatized alginic acid antigen (▨); O-acetylated antigen (□); or O-propionylated antigen (▨)
Figure 8B:
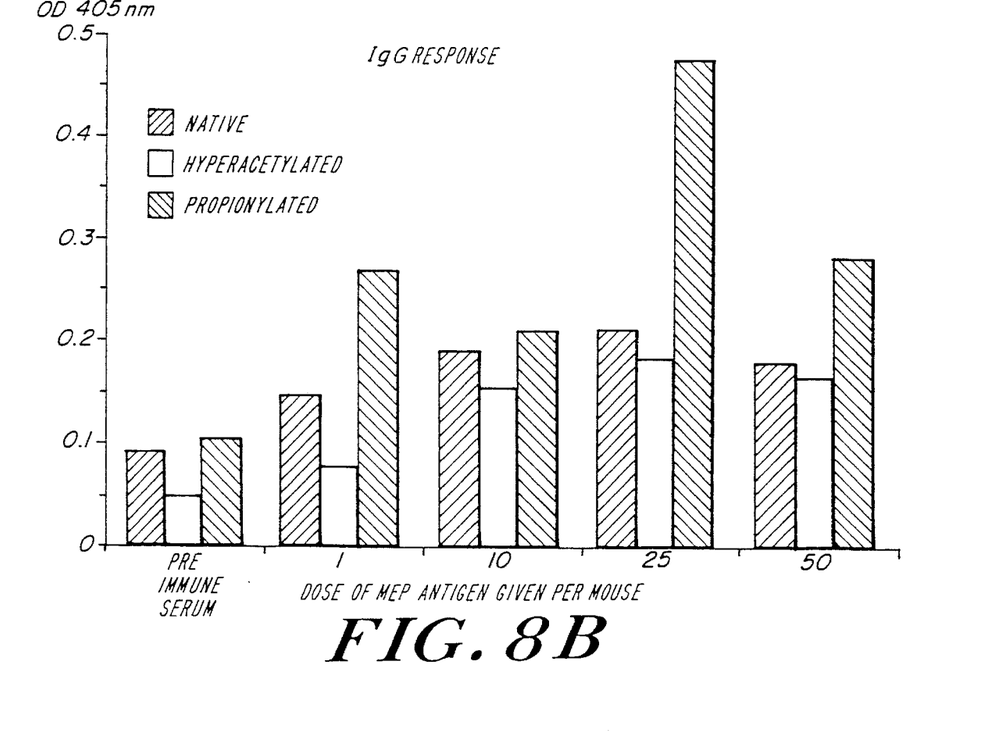
Figure 9A:
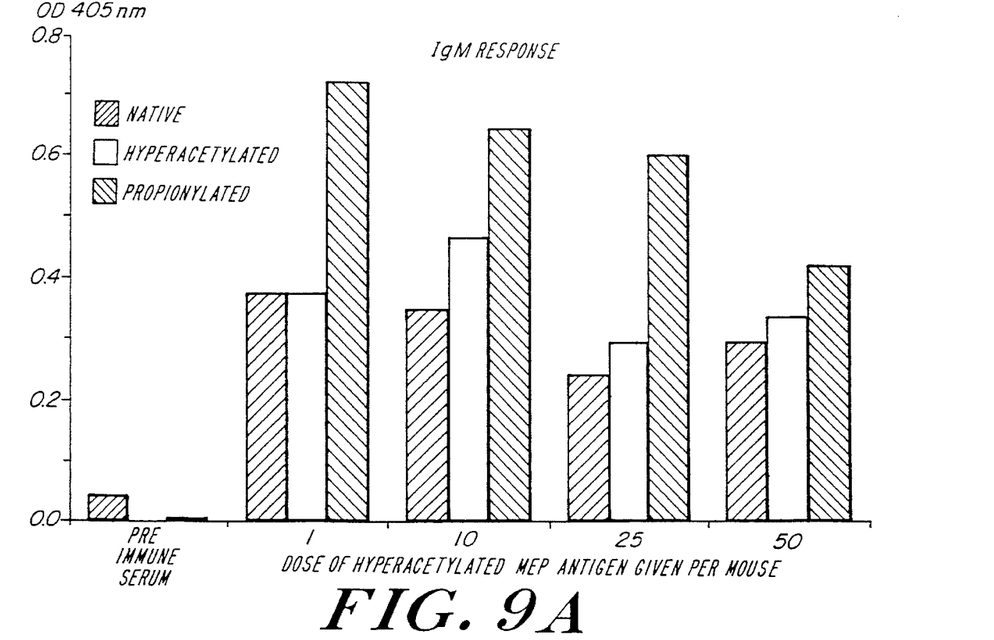
FIG. 9A and 9B are graphs that illustrate antigenicity of mouse antibodies elicited by O-acetylated MEP alginic acid antigen; the symbols are identical to those used in FIGS. 8A and 8B.
Figure 9B:
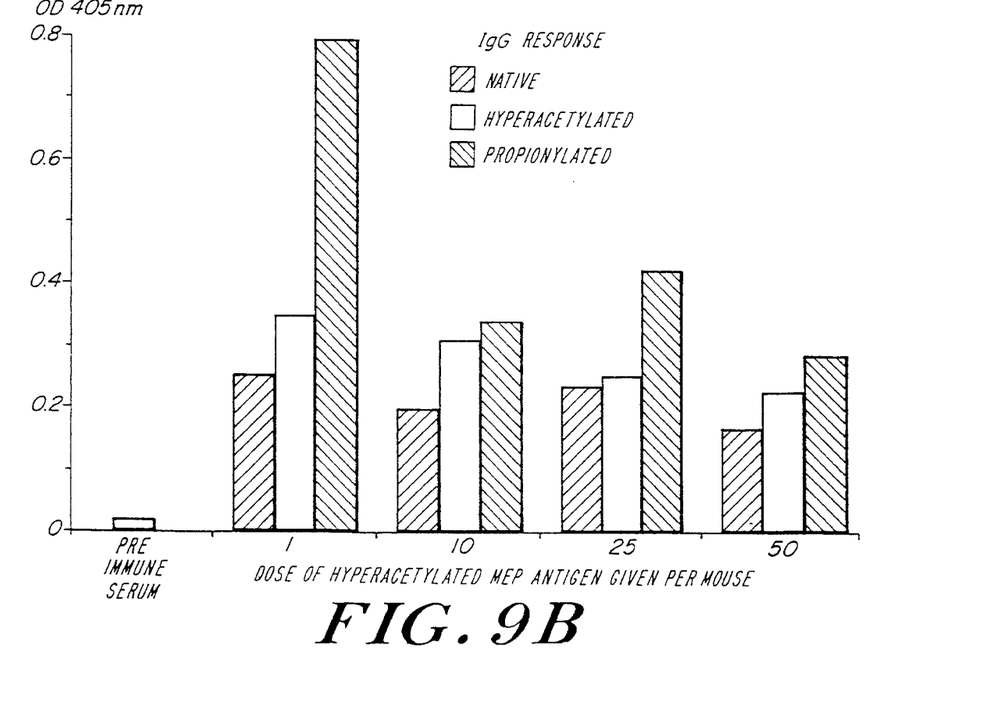
Figure 10A:
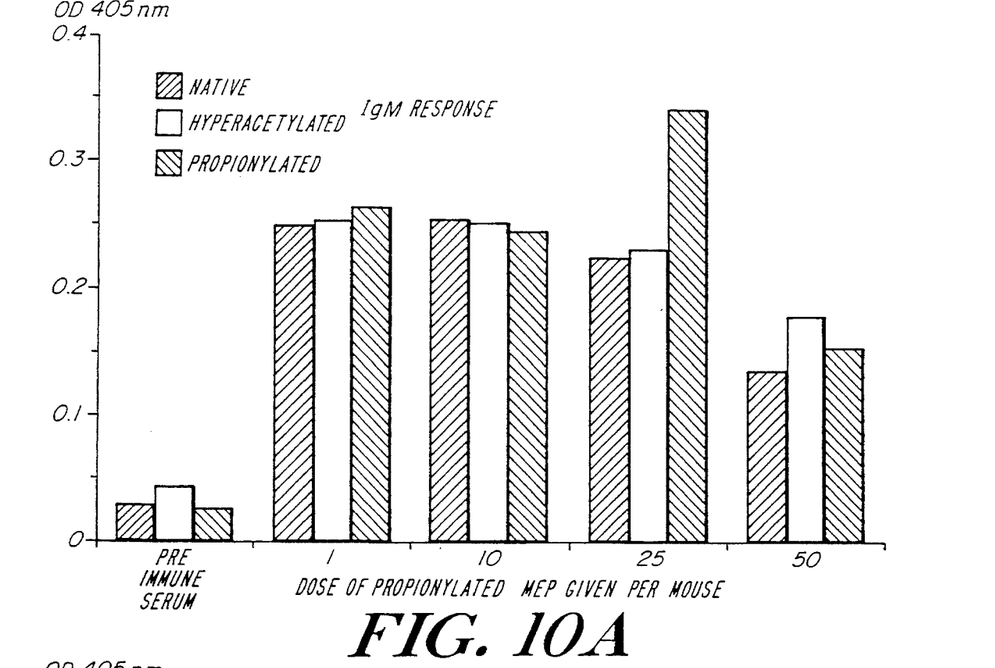
Figure 10B:
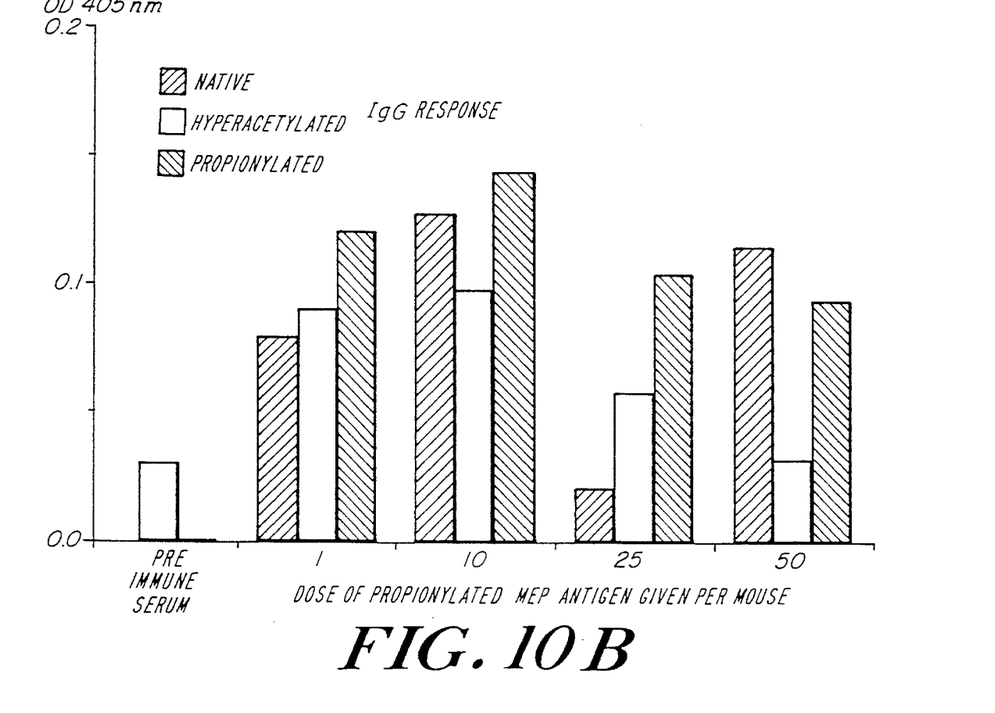

These data show again that O-propionylated antigen provoked greater levels of killing than the other preparations.

ii. Antigenicity analysis. Antigenicity of the antibodies elicited by immunization was tested in the ELISA assay using the protocol described above. The ELISA measures all antibodies, both opsonic and nonopsonic. The biologically important ones are the opsonic killing antibodies, measured above in the phagocytosis assay. FIGS. 8–10 show the results. The upper section of each graph shows the IgM response; the lower section shows the IgG response;.

Mice were immunized twice on days 0 and 14 with either native MEP antigen, O-acetylated MEP, or O-propionylated MEP (FIGS. 8, 9, and 10, respectively). In general, using mouse sera the O-acetylated, and especially the O-propionylated, MEP preparation gave a higher binding of antibody compared to the native, non-O-derivatized MEP antigen. We have noted that the O-propionylated preparation routinely works better with human antibodies, but with mouse antibodies it is sometimes superior and sometimes not. The enhanced binding of antibodies to the O-derivatized MEP preparations was usually observed regardless of the immunizing preparation.

EXAMPLE 3

Antigen Prepared from Seaweed

As used in this example, "seaweed alginic acid" means commercially available alginic acid, isolated from seaweed, and composed of the sugars mannuronic acid and guluronic acid. The preparation used in the experiments described below had a ratio of about 1:1 of these two sugars. This is in contrast to "native MEP", which is used in this example to mean mucoid exopolysaccharide antigen isolated from the bacterium Pseudomonas aeruginosa. Native MEP also is composed of the sugars mannuronic acid and guluronic acid, and the preparation used in the experiments below had a ratio of about 4:1 mannuronic acid to guluronic acid.

In the experiments described below, the following terms have the following meanings:

BSA: bovine serum albumin, carrier protein covalently coupled to native alginic acid;

Carbodiimide: water soluble carbodiimide, a Chemical agent for coupling alginic acid to free amino groups by activating the carboxylate group on the uronic acid;

Periodate: sodium metaperiodate, a chemical agent used to oxidize alginic acid as part of a coupling procedure;

ELISA™: Enzyme Linked Immunosorbent Assay used to measure antibody levels;

IgG: mouse serum immunoglobulin G antibodies;

IgM: mouse serum immunoglobulin M antibodies.

Seaweed alginic acid was coupled to BSA using either water soluble carboxiimide [Taylor, R. L. et al., 1972, *Biochemistry* 11:1383–8; Beuvery, E. C. et al., 1986, *Dev. Biol. Stand.* 63:117–28; Bauminger, S., et al., 1980, Methods Enzymol. 70:151–9] or the periodate/sodium cyanoborohydride method [Wessels, M. R. et al., 1990, *J. Clin. Invest.* 86:1428–1433; Paoletti, L. C. et al., 1992, *Infect. Immun.* 60:4009–14]. After the coupling reaction was completed the large sized conjugates were separated from the smaller sized unconjugated fractions by chromatography over a molecule sieve column. The larger sized, early diluting material was recovered, fractions pooled, dialyzed against water and lyophilized.

The conjugate was then acetylated on free hydroxyl groups (O-derivatized) as described above in the specification by suspending the conjugate in a 1:1 volume ratio of pyridine and acetic anhydride. This was stirred at room temperature for 48 hours after which water was added. The preparation then was dialyzed against water and lyophilized.

The two different conjugates (referred to as carbodiimide coupled and periodate coupled) were administered to groups of C3H/HeN female mice, 6 weeks of age, (3 mice per group) at doses of 1, 10, 25 or 50 μg per mouse. Doses were given on day 0, day 7 and day 14. Sera was collected for antibody analysis on days 14, 28, 35 and 42.

Sera were tested by ELISA™. A serum dilution of 1:5 was used to measure IgG antibodies and a dilution of 1:20 used to measure IgM antibodies. Antibodies were measured against seaweed alginic acid and native MEP (representing non-O-derivatized and O-derivatized antigens, respectively). Standard ELISA™ protocols were used.

The optical density readings at the end of the ELISA™ was made and then the reading corrected for the amount of activity in the preimmunization serum by subtracting out this value.

Data was as follows:

The higher the OD the more antibody found. In general, the higher the dose, the more antibody found. Most readings were maximal on day 42 (some exceptions), 3 weeks after the final dose on day 14. Both IgG and IgM readings were higher when tested against the native MEP than against "seaweed alginic acid". IgG levels to native MEP were higher with the periodate coupled preparation compared with the carbodiimide coupled preparation, particularly on days 28, 35 and 42.

Given that the IgG antibodies to native MEP are the desired results of this vaccine preparation methodology, the periodate-coupled preparation elicited excellent antibody responses, meaning that by O-derivatizing the seaweed alginic acid, one can produce an antigen that elicits antibodies to a bacterial antigen (native MEP in this case).

Those skilled in the art will be able to ascertain, using no more than routine experimentation, many equivalents of the specific embodiments of the invention described herein. These and all other equivalents are intended to be encompassed by the following claims.

I claim:

1. An O-derivatized alginic acid antigen comprising
   a backbone of a uronic acid polymer including D-mannuronic acid, wherein said uronic acid polymer is derivatized with a nonacetyl short chain carboxylic acid.

2. An O-derivatized alginic acid antigen as claimed in claim 1, wherein the uronic acid polymer also includes guluronic acid and the short chain carboxylic is selected from the group consisting of propionic acid, butyric acid, isobutyric acid, valeric acid and isovaleric acid.

3. An O-derivatized alginic acid antigen as claimed in any one of claims 1 and 2 wherein the uronic acid polymer is derivatized also with acetic acid.

4. An O-derivatized alginic acid antigen as claimed in claim 3 wherein the uronic acid polymer is a *Pseudomonas aeruginosa* mucoid exopolysaccharide.

5. An O-derivatized alginic acid antigen as claimed in claim 3 wherein the uronic acid polymer is a seaweed uronic acid polymer.

6. An O-derivatized alginic acid antigen as claimed in claim 3 wherein the antigen is derivatized between about 2% and 12% by weight with short chain carboxylic acid.

7. An O-derivatized alginic acid antigen as claimed in claim 3 further comprising a protein covalently linked to said uronic acid polymer.

8. An O-derivatized alginic acid antigen as claimed in claim 3, wherein the antigen is formulated as a vaccine for a human.

9. An O-derivatized alginic acid antigen comprising a backbone of a uronic acid polymer including L-guluronic and D-mannuronic acids, wherein said uronic acid polymer is derivatized with a short chain carboxylic acid on a plurality of L-guluronic acid moieties.

10. An O-derivatized alginic acid antigen as claimed in claim 9 wherein the short chain carboxylic acid is selected from the group consisting of acetic acid, propionic acid, butyric acid, isobutyric acid, valeric acid and isovaleric acid.

11. An O-derivatized alginic acid antigen as claimed in claim 10 wherein the short chain carboxylic acid is selected from the group consisting of propionic acid, butyric acid, isobutyric acid, valeric acid and isovaleric acid.

12. An O-derivatized alginic acid antigen as claimed in claims 10 or 11 wherein the uronic acid polymer is derivatized with acetic acid on a plurality of D-mannuronic moieties.

13. An O-derivatized alginic acid antigen as claimed in claim 12 wherein the uronic acid polymer is a *Psuedomonas aeruginosa* mucoid exopolysaccharide.

14. An O-derivatized alginic acid antigen as claimed in claim 12 wherein the uronic acid polymer is a seaweed uronic acid polymer.

15. An O-derivatized alginic acid antigen as claimed in claim 12 wherein the antigen is derivatized between about 2% and 12% be weight with short chain carboxylic acid.

16. An O-derivatized alginic acid antigen as claimed in claim 12 wherein the antigen is formulated as a vaccine for a human.

17. An O-derivatized alginic acid antigen as claimed in claim 12, further comprising a protein covalently linked to said uronic acid polymer.

18. An O-derivatized alginic acid antigen comprising a backbone of a uronic acid polymer including L-guluronic acid and D-mannuronic acid, wherein the L-guluronic acid is present in blocks and wherein the antigen is derivatized with short chain carboxylic acids that are present between about 2% and 12% by weight.

19. An O-derivatized alginic acid antigen as claimed in claim 18 wherein at least some of the short chain carboxylic acid is selected from the group consisting of propionic acid, butyric acid, isobutyric acid, valeric acid and isovaleric acid.

20. An O-derivatized alginic acid antigen as claimed in claim 19 further comprising a protein covalently linked to the uronic acid polymer.

21. An O-derivatized alginic acid antigen as claimed in claim 19 wherein the antigen is formulated as a vaccine for a human.

22. A method for preparing an antigen capable of eliciting an immune response characterized by the production of antibodies that bind to a *Pseudomonas aeruginosa* mucoid exopolysaccharide comprising derivatizing hydroxyl groups of a uronic acid polymer with a short chain carboxylic acid selected from the group consisting of acetic acid, propionic acid, butyric acid, isobutyric acid, valeric acid and isovaleric acid.

23. A method as claimed in claim 22 wherein the uronic acid polymer includes D-mannuronic and L-guluronic acids, and wherein hydroxyl groups of L-guluronic acid moieties are derivatized with said short chain carboxylic acid.

24. A method as claimed in claim 22 wherein the uronic acid polymer is a *Pseudomonas aeruginosa* mucoid exopolysaccharide.

25. A method as claimed in claim 22 further comprising at least partially deacetylating *Pseudomonas aeruginosa* mucoid exopolysaccharide prior to said derivatization step.

26. A method as claimed in claim 22 wherein the uronic acid polymer is a seaweed uronic acid polymer.

27. A method as claimed in claim 22 further comprising first forming the uronic acid polymer by covalently attaching a plurality of D-mannuronic acids or blocks thereof to a plurality of L-guluronic acids or blocks thereof.

28. A method as claimed in claim 22 wherein at least some of said short chain carboxylic acid is selected from the group consisting of propionic acid, butyric acid, isobutyric acid, valeric acid and isovaleric acid.

29. A method as claimed in claim 22 further comprising covalently attaching a protein to said uronic acid polymer.

* * * * *